United States Patent [19]

Katzir et al.

[11] Patent Number: 5,008,743
[45] Date of Patent: Apr. 16, 1991

[54] TELECENTRIC IMAGING SYSTEM OPTICAL INSPECTION MACHINE USING THE SAME AND METHOD FOR CORRECTING OPTICAL DISTORTION PRODUCED THEREBY

[75] Inventors: Yigal Katzir, Holon; Joseph Kochba, Yavne, both of Israel

[73] Assignee: Orbot Systems Ltd., Yavne, Israel

[21] Appl. No.: 324,716

[22] Filed: Mar. 17, 1989

[30] Foreign Application Priority Data

Mar. 24, 1988 [IL] Israel .......................................... 85862

[51] Int. Cl.⁵ ............................................. H04N 7/18
[52] U.S. Cl. .................................... 358/101; 358/107; 358/225; 350/415
[58] Field of Search ................... 358/100, 107, 101, 93, 358/88, 225, 106; 350/415, 452

[56] References Cited

U.S. PATENT DOCUMENTS

| | | | |
|---|---|---|---|
| 3,637,282 | 1/1972 | Hayamizu et al. | 350/415 X |
| 3,761,184 | 9/1973 | McLaughlin, Jr. | 350/415 X |
| 3,994,583 | 11/1976 | Hutchins, IV | 350/415 X |
| 4,582,393 | 4/1986 | Shieman | 358/91 X |
| 4,695,892 | 9/1987 | Mary | 358/107 X |
| 4,851,913 | 7/1989 | Fetzer et al. | 358/101 X |

*Primary Examiner*—Victor R. Kostak
*Attorney, Agent, or Firm*—Sandler, Greenblum & Bernstein

[57] ABSTRACT

A telecentric imaging system includes a Fresnel lens mountable in proximity to an object to be imaged, a source of light for illuminating the object, and an aperture stop located at least in the telecentric imaging system is incorporated into an optical inspection machine which permits optical distortion produced by the telecentric imaging system to be corrected using a look-up table.

10 Claims, 9 Drawing Sheets

Y-AXIS DISTORTION CALIBRATION

Translate optical head 34 along x-axis so as to bring at least some segment of target edge 36 into the "swath" cut by camera 10, in proximity to one edge of the "swath". Choose some arbitrary camera 10 resolution element $q_0$ and monitor the signal at element $q_0$ as the object stage is scanned continuously along y-axis. Element $q_0$ senses x-coordinate $x^0$ on object stage, properly accounting for x-axis distortions.

Use camera 10 signal to compute the instant of time edge 36 is sensed by camera $q_0$. Since camera 10 signal is synchronized with object stage motion, use timing signals to determine the corresponding apparent edge y-coordinate $y^0$.

$m = 1$

Translate column 34 by fixed, precisely known but otherwise arbitrary distance S, corresponding to an integral number k of pixels (using previously computed actual coordinates). Some edge point at $x = x^0$ is now sensed by a new camera resolution element $q_m = q_p + mk$ at some instant of time as the object stage is continuously scanned along y-axis.

Use camera 10 signal at element $q_m$ in combination with object stage position signal to determine the apparent, possibly distorted edge 36 y-coordinate $y^m$ as sensed by element $q_m$.

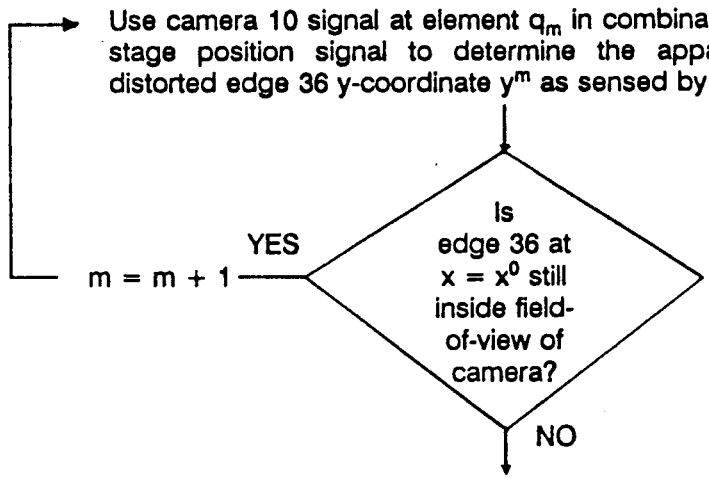

Plot the array of camera element numbers $q_0, q_1, \ldots, q_m$ against the set of corresponding y-axis coordinates $Y^0, Y^1, \ldots, Y^m$.

Perform a linear regression on resulting set of measured points, using a suitable curve fitting algorithm.

Compute y-axis deviations $\Delta Y^0, \Delta Y^1, \ldots, \Delta Y^m$ of measured points from the ideal regression line.

Interpolate the y-axis deviations for all camera 10 resolution.

FIG. 9B

TELECENTRIC IMAGING SYSTEM OPTICAL INSPECTION MACHINE USING THE SAME AND METHOD FOR CORRECTING OPTICAL DISTORTION PRODUCED THEREBY

The present invention relates to a telecentric imaging system, in particular for use with an optical inspection machine and capable of exactly reproducing the contours of three-dimensional objects. It also relates to an optical inspection machine of the scanning type employing such a system and a method for software correction of the optical distortion produced by the above system.

Optical inspection machines usually incorporate some type of imaging system. The imaging system very often includes a lens system and some type of camera. In such systems the lens forms an image of an input plane, where the workpieces are located into an output plane, usually that plane which is recorded by the camera.

A typical application of optical inspection is the dimensional measurement of opaque objects. In such applications, the objects to be measured are usually back illuminated to obtain high contrast. The primary requirement on the lens system in such applications is to form a geometrically precise image of the contour of the part under inspection. With a good quality imaging lens, that requirement is usually easily fulfilled for any workpiece that is essentially flat (two dimensional).

A particular problem arises when the inspected part has depth (three dimensional). In that case, the contour image generally depends on the location of the object within the field of view of the imaging optics, thus giving rise to undesirable ambiguity of the test results.

A well known solution to the above ambiguity problem is to use a telecentric imaging system which has its entrance pupil located at infinity. In such a system the principal ray emanating from each object point is parallel to the optical axis. Consequently, all object points within a finite field of view are observed with the same perspective. Such a telecentric system should have a front element (the one nearest the object) that is at least as large as the designated field of view. If this optical element is a conventional lens, as is usually the case, it may become excessively large and heavy to allow an extended field of view. Furthermore, unless the lens is mounted in close proximity to the object, it also needs to be of good optical quality, and is therefore fairly expensive. Even so, conventional lenses generally introduce some undesirable field curvature.

It is an object of the present invention to overcome the drawbacks and disadvantages of prior-art imaging systems, and to provide a telecentric imaging system that is simpler and less expensive than conventional systems, and uses as front element a relatively inexpensive, thin and light optical element inherently free of field curvature.

This, according to the invention, is achieved by providing a telecentric imaging system, comprising a Fresnel lens mountable in proximity to an object to be imaged, a source of light for illuminating said object, and an aperture stop located at least in vicinity of the back focal point of said Fresnel lens.

The invention further provides an optical inspection machine of the line-scanning type employing a telecentric imaging system, comprising a column capable of translatory movement, an object stage capable of translatory movement in a direction substantially perpendicular to the translatory movement of said column, a transparent window on said object stage, means to mount said object on said window, an extended source of light behind said window a line-scanning camera mounted on the head of said column, an objective lens adapted to image said object on the sensor plane of said camera, a field lens, optically coaxial with said objective lens and located in proximity to said object to be imaged and an aperture stop for said field lens wherein said field lens is a Fresnel lens, said aperture stop is located at the back focal point of said Fresnel lens and is constituted by the entrance pupil of said imaging objective, whereby the system objective/field lens is rendered telecentric.

The invention still further provides a method for software correction of the optical distortion produced by a telecentric imaging system including a line-scanning camera and a Fresnel lens, comprising the steps of mounting on an object stage of said system a calibration target comprising at least one reference mark and effecting a relative translation between said camera and said object stage in the direction of a first and a second of two intersecting axes, until said reference mark is imaged on, and sensed by said camera, calculating, from the signal produced by said camera, the camera element upon which said reference mark is imaged, and effecting a relative translatory motion between said camera and said object stage along said first axis in discrete, equal and precisely known steps, and sensing said reference mark at each step, plotting the thus established set of camera elements against the sequence of said discrete steps, and performing on the points thus plotted a linear regression establishing, using the regression line thus obtained, as set of first axis deviations and entering said deviations in a look-up table to be used to correct subsequent camera signals, effecting a continuous translatory motion between said camera and said object stage in direction of said second axis until said reference mark is imaged on, and sensed by said camera, calculating from the signal produced by said camera, the camera element upon which said reference mark is imaged and the corresponding coordinate along second axis effecting a relative translatory motion between said camera and said object stage in direction of said first axis in discrete, equal and precisely known steps, effecting a continuous, relative translatory motion between said camera and said object stage in direction of said second axis, following each of said first-axis translations, and sensing said reference mark at each step plotting the thus established set of camera elements against the corresponding second-axis coordinates, and performing on the points thus plotted a linear regression, and establishing, using the regression line thus obtained, a set of second axis deviations and entering said deviations in a look-up table to be used to correct subsequent camera signals.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 5:
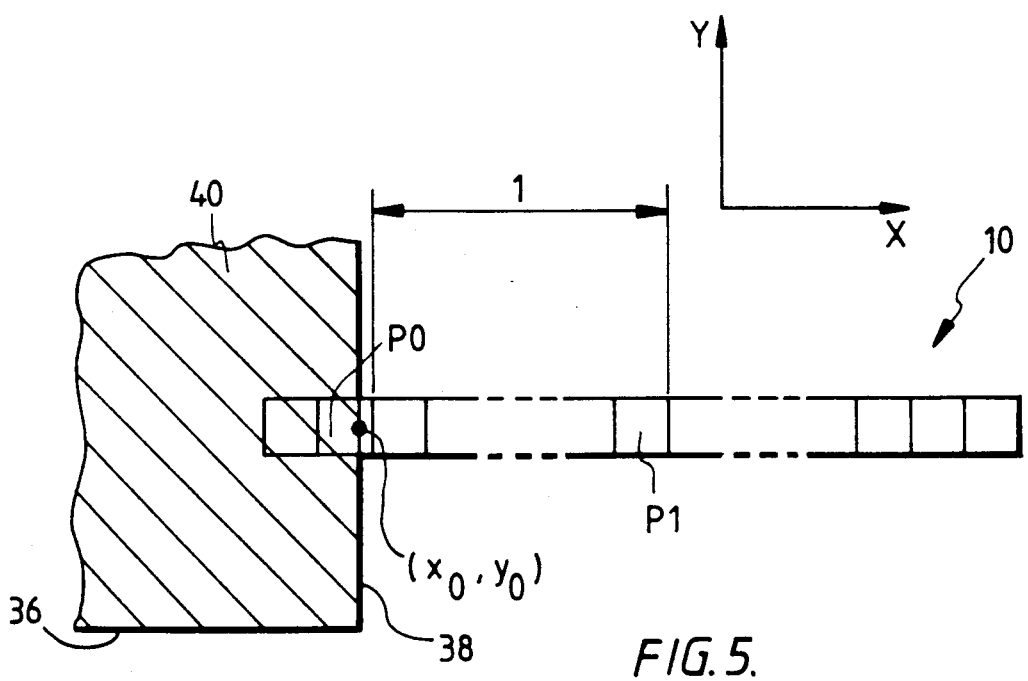
Figure 6A:
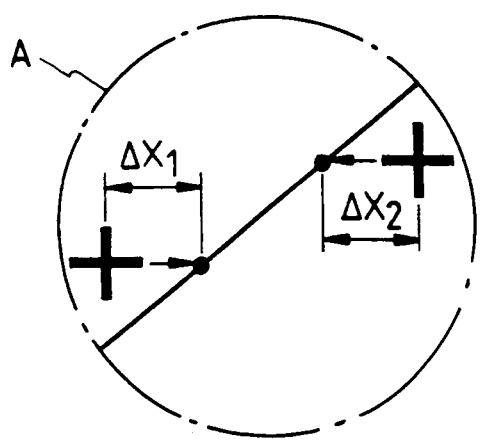
Figure 6:
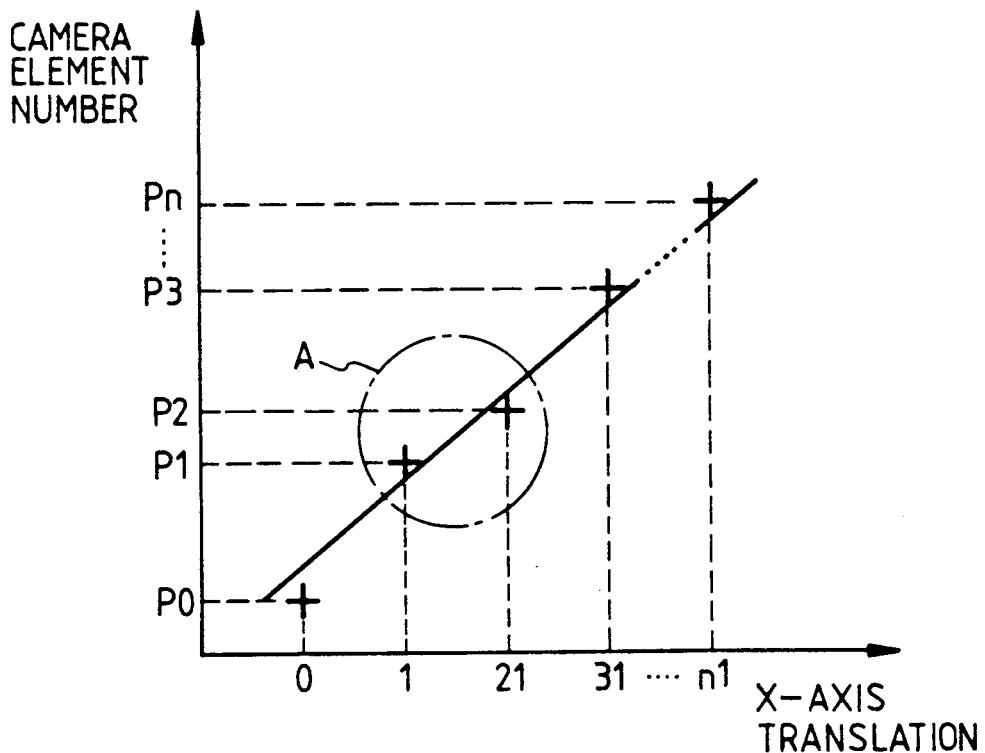
Figure 7:
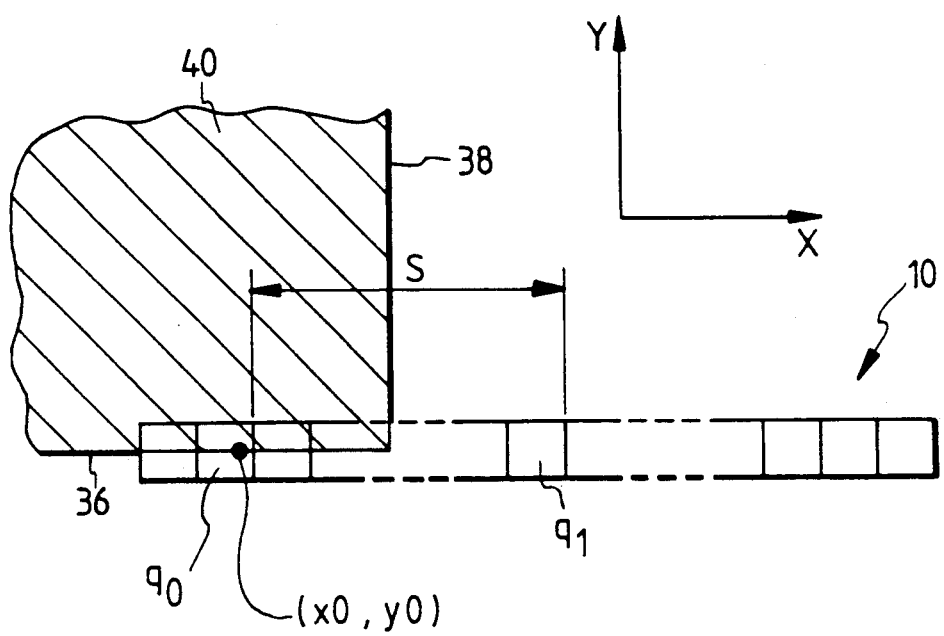
Figure 8A:
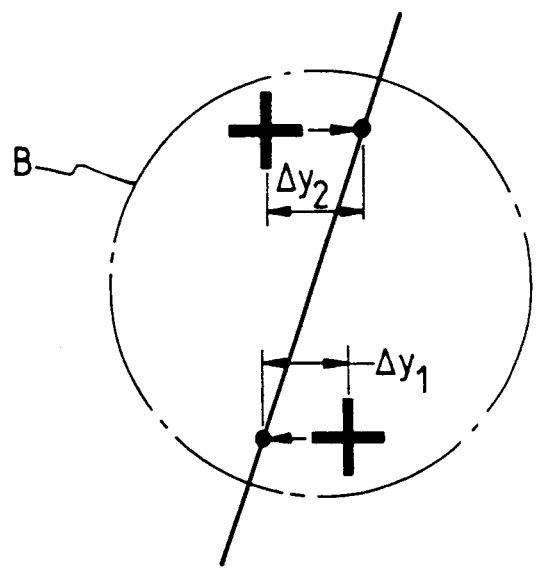
Figure 8:
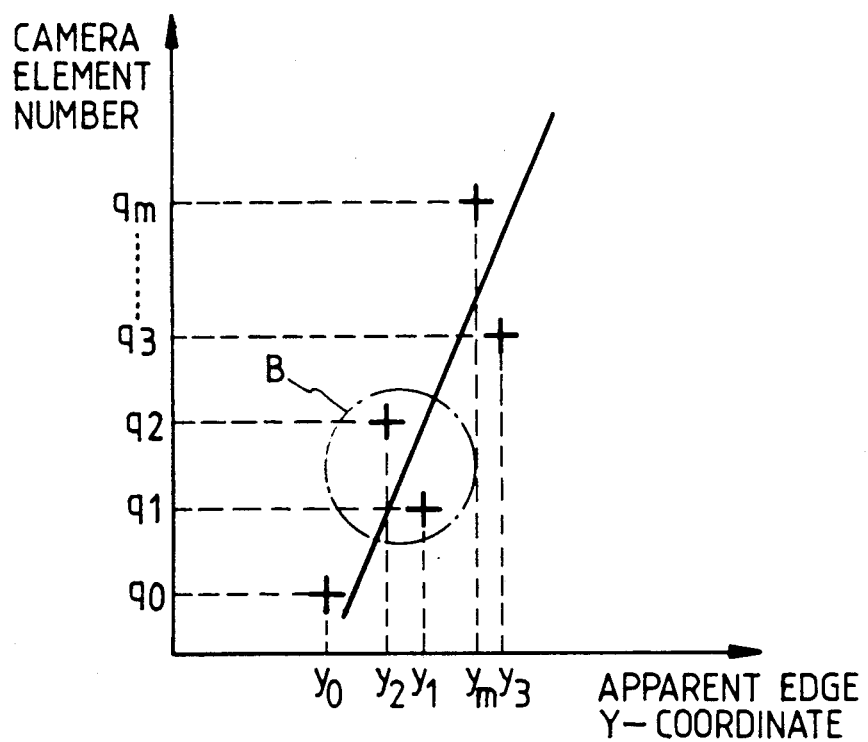
Figure 9A:
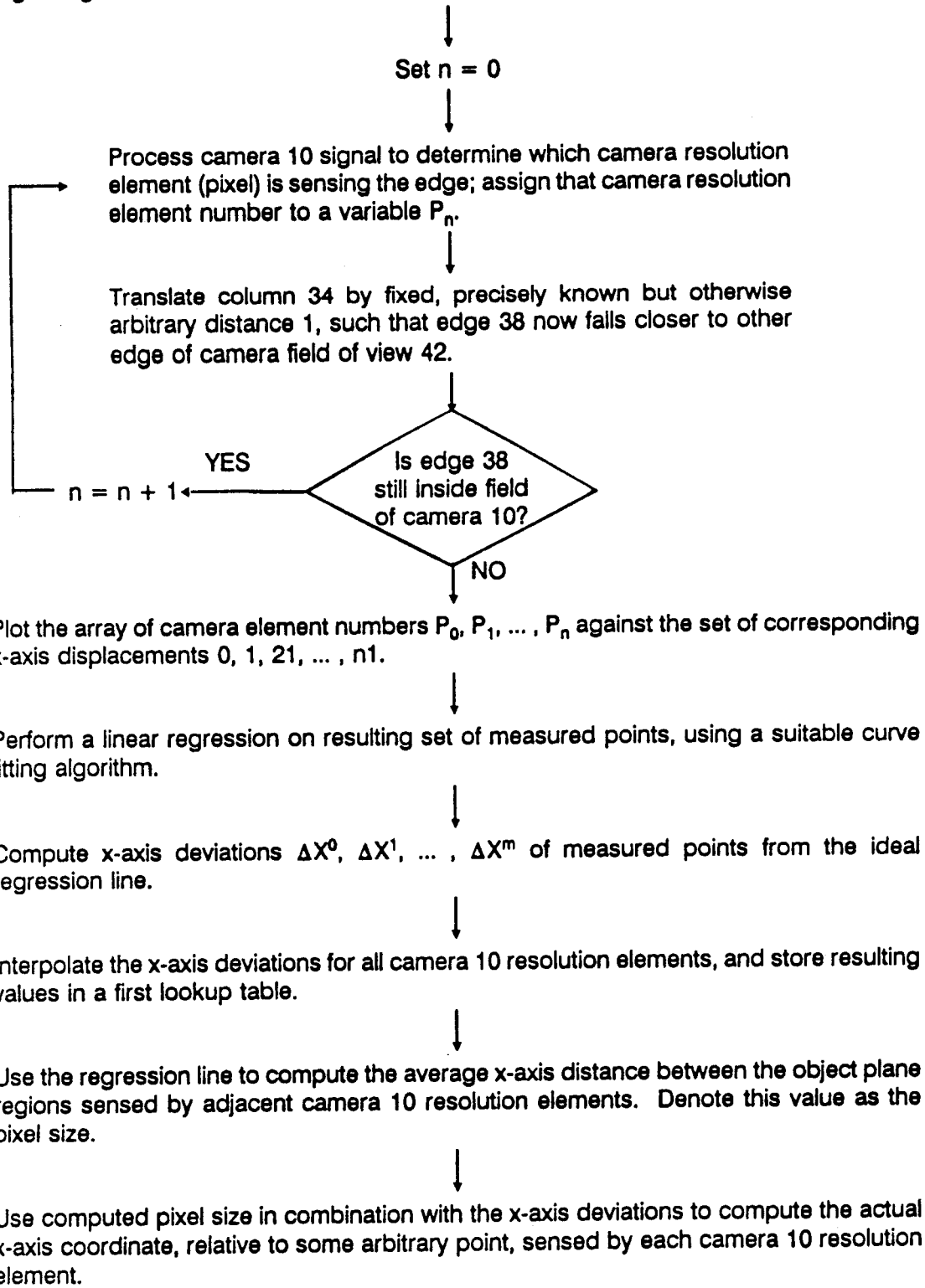

FIG. 5 schematically illustrates the first stage of the correction method according to the invention:

FIG. 6 is a diagram showing the plotted results of the first stage of the correction method;

FIG. 6A is an enlarged representation of the detail A of FIG. 6;

FIG. 7 schematically illustrates the second stage of the correction method according to the invention;

FIG. 8 is a diagram showing the plotted results of the second stage of the correction method, FIG. 8A is an enlarged representation of the detail B of FIG. 8, FIG. 9A is a flow chart that shows the steps involved in carrying out an X-axis distortion calibration according to the present invention; and FIG. 9B is a flow chart that shows the steps involved in carrying out an Y-axis distortion calibration according to the present invention.

Figure 1:
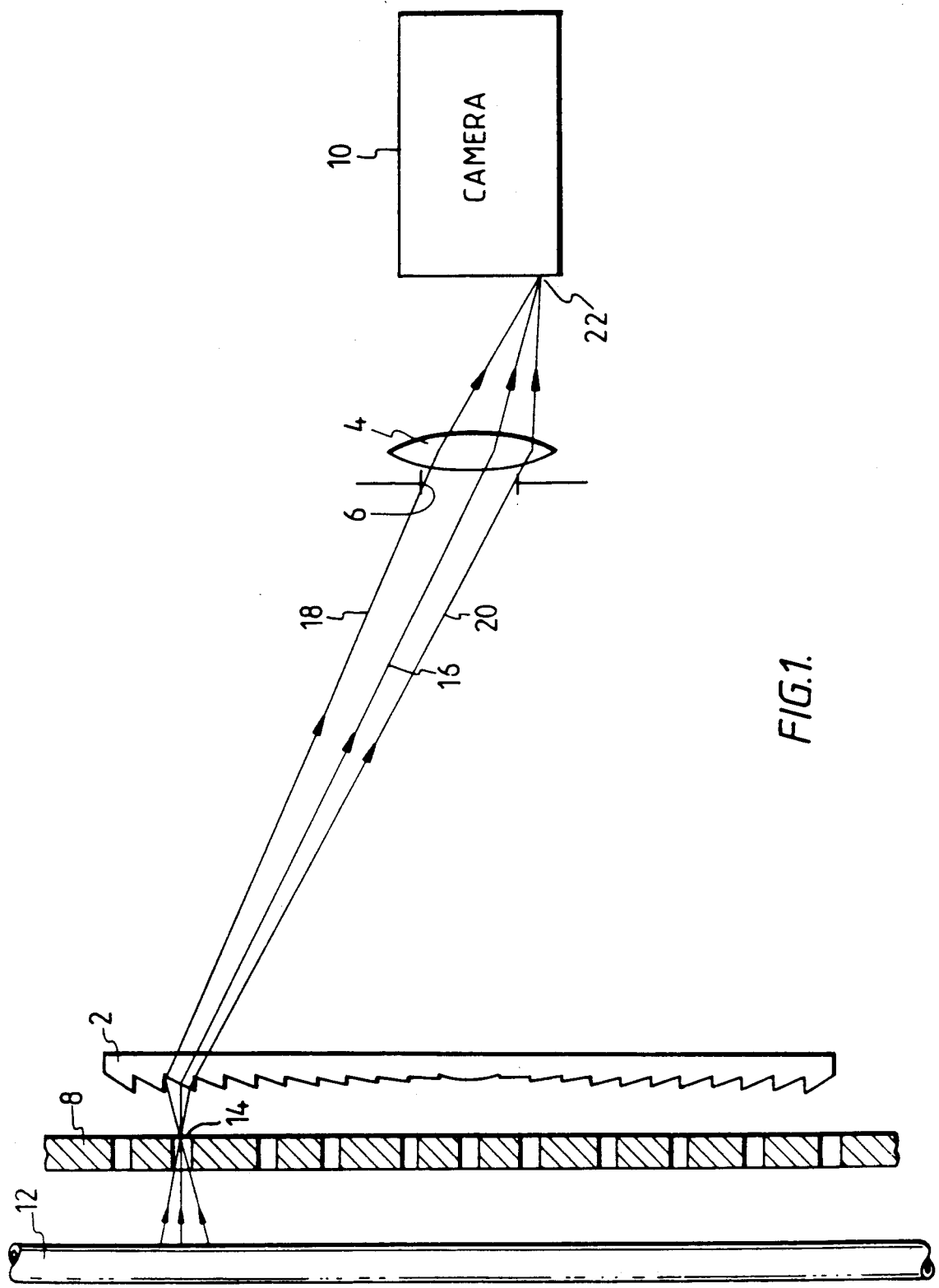
FIG. 1 is a schematic diagram representing the major elements comprising the improved telecentric system and their interrelationship. also showing a typical light path.

Referring now to the drawings, there is shown in FIG. 1 the telecentric system according to the invention, as comprised of two components, one of which is a Fresnel lens 2 advantageously made of a plastic material, and the other a good quality imaging lens 4 that is well corrected for operation at a finite conjugate ratio. The entrance pupil of imaging lens 4 is symbolically represented as 6 in FIG. 1. The center of this entrance pupil is located in the vicinity of the back focal point of the Fresnel lens 2 thus turning the physical aperture of lens 4 into the telecentric aperture stop of the Fresnel lens 2.

The optical imperfections found with the relatively cheap plastic Fresnel lenses are correctable by a software correction method explained further below.

The Fresnel lens 2 is mounted in close proximity to the printed circuit board 8, in the sense that the distance between lens and board is small relative to the focal length of the Fresnel lens. The diameter of the Fresnel lens 2 is at least equal to the designated field of view of the system. The Fresnel lens 2 and imaging lens 4 are positioned so as to form an image of the surface of printed circuit 8 on the sensor plane of camera 10. The drilled printed circuit board 8 is back-illuminated by an extended source 12 e.g., a fluorescent lamp.

FIG. 1 also illustrates light paths from an arbitrary point 14 inside the bore of a drilled hole, to the corresponding image point 22. Ray 16 is the principal ray, i.e., the one passing through the center of the aperture stop whereas rays 18 and 20 are marginal rays. It should be noted that the system is telecentric in object space only, where the Principal rays are all parallel to the optical axis. Consequently, all drilled holes are imaged parallel to their bore, so that their apparent contour is independent of their position within the field of view.

Figure 2:
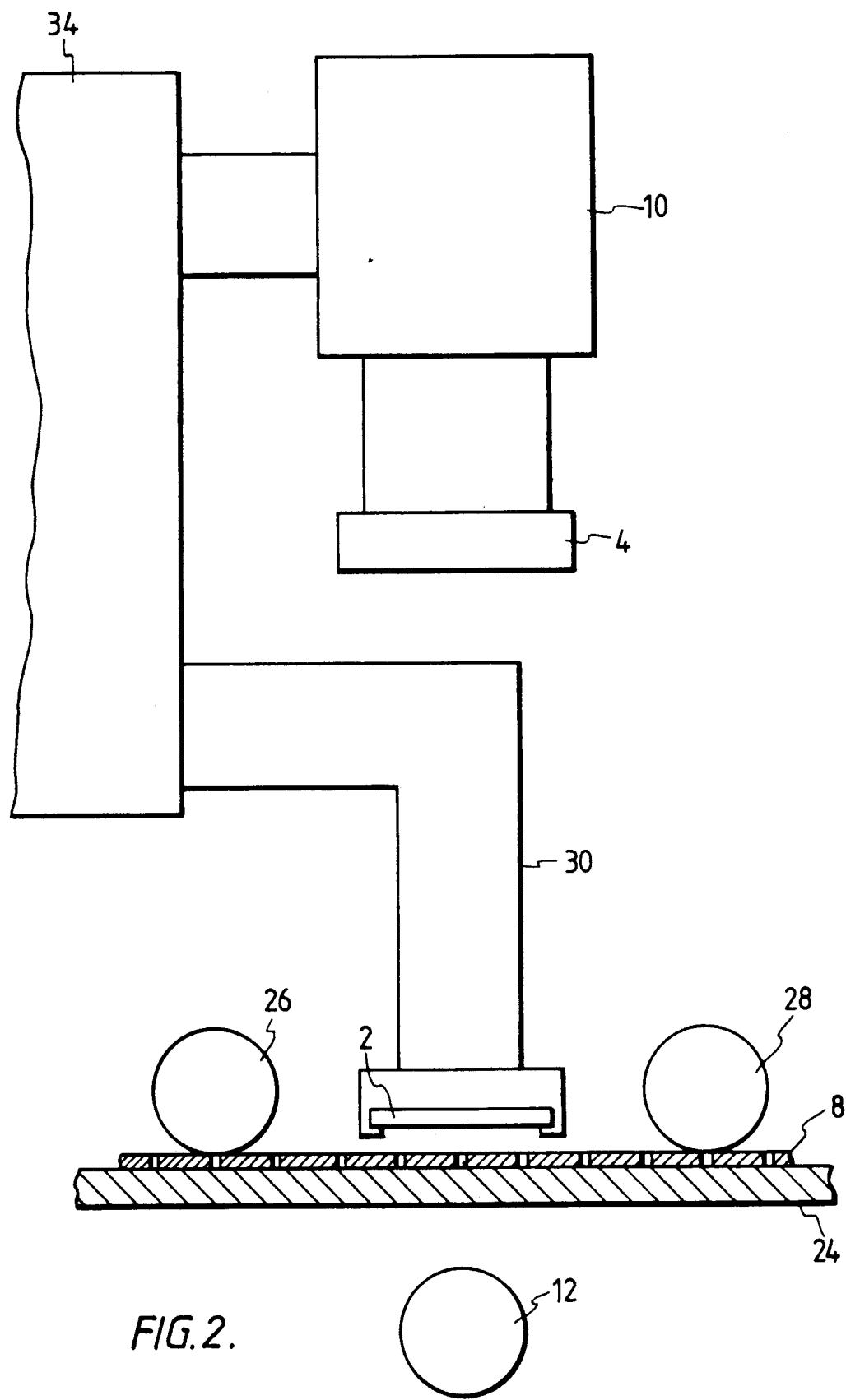
FIG. 2 is a side view of the system as incorporated in an optical scanner for inspection of drilled printed circuit boards.
Figure 3:
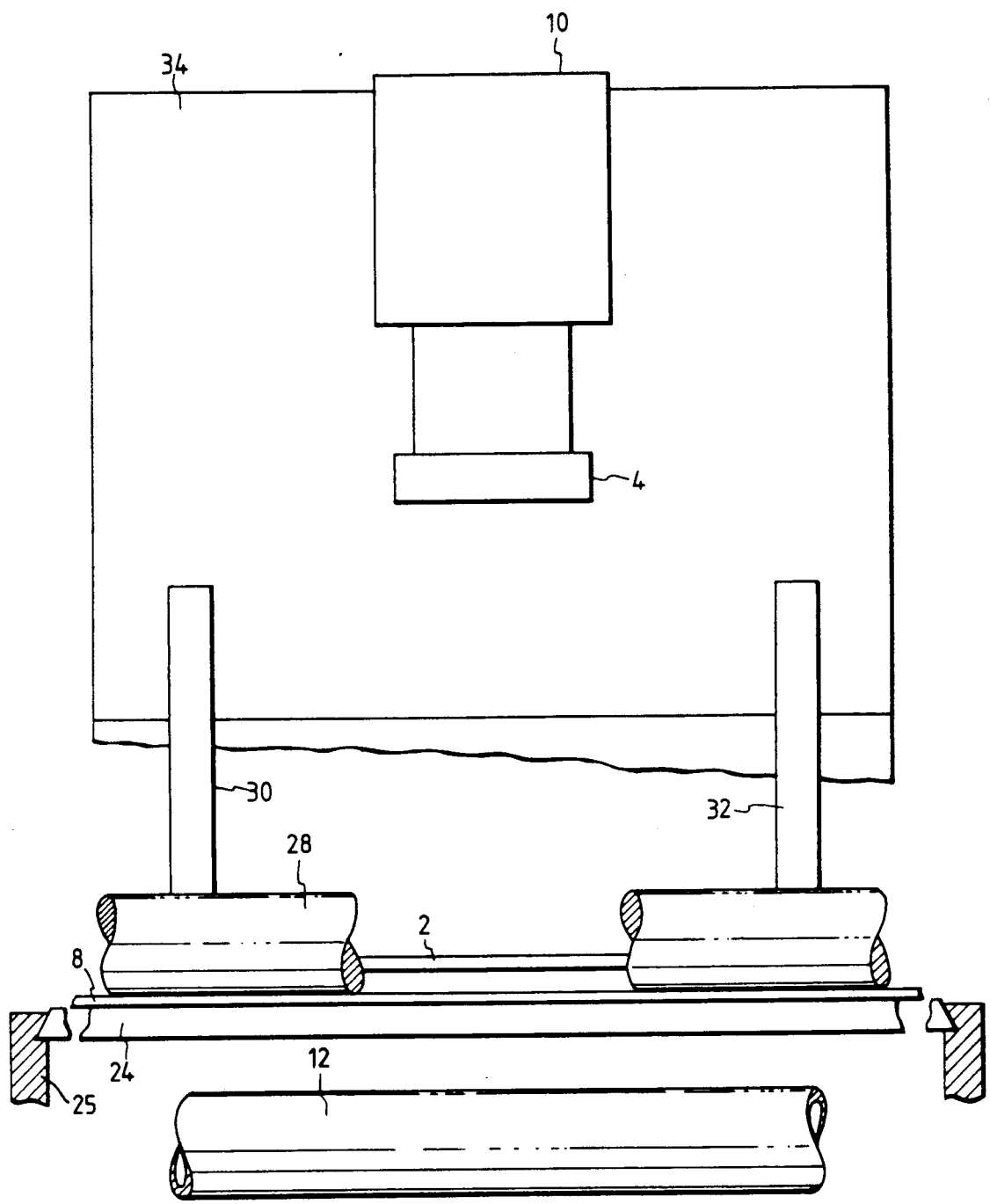
FIG. 3 is a front view of the above optical scanner.

FIGS. 2 and 3 illustrate a scanning system provided with the imaging system according to the invention. The scanning system employs, for example, a rectilinear line-scan CCD camera 10, with the scanned line extending in a plane perpendicular to the plane of FIG. 2, and parallel to the plane of FIG. 3. The printed-circuit board to be inspected is mounted on the transparent window 24 of a translating stage 25, with two spring-loaded rollers 26, 28 pressing the board against the window 24. The stage translates the PC-board 8 in the plane of the paper in FIG. 2 and into the paper, in FIG. 3.

The plastic Fresnel lens 2 is a narrow slab cut from the central part of the original lens, and held rigidly in a position substantially parallel to the line scanned by the camera by two supporting members 30, 32.

The Fresnel lens 2 is mounted in such a way that its optical axis substantially coincides with that of imaging lens 4.

Figure 4:
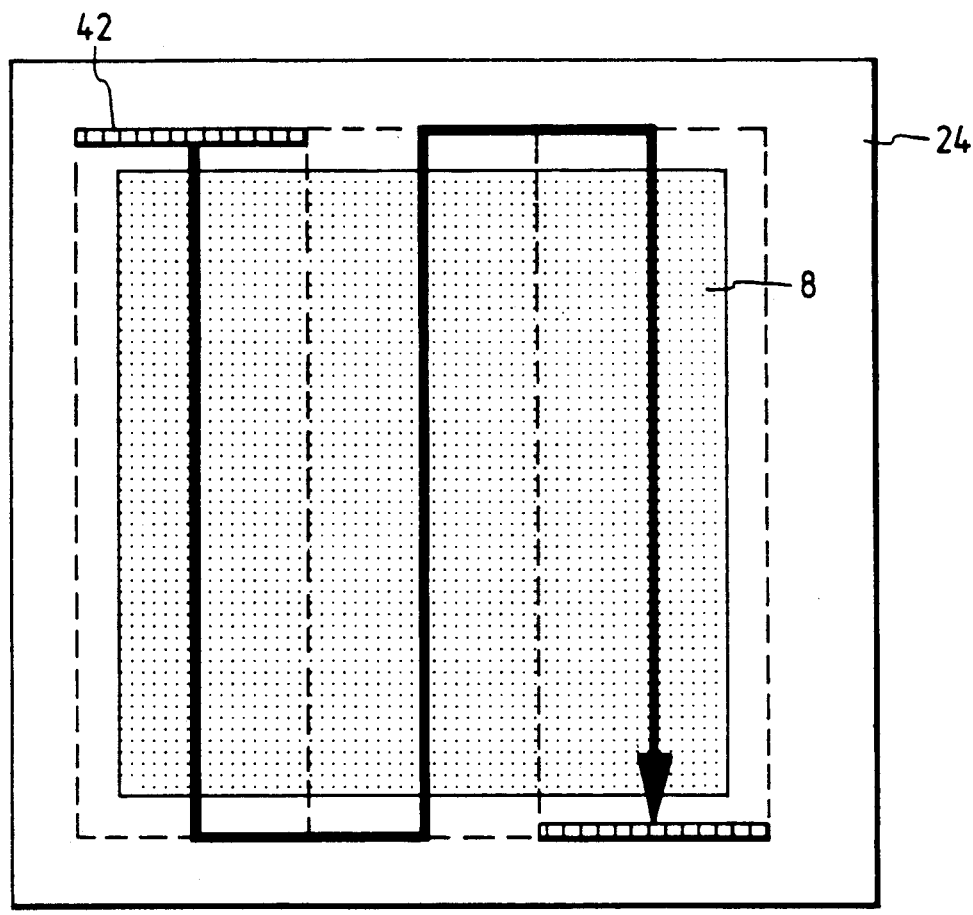
FIG. 4 is a schematic illustration of the inspection pattern of the line-scan camera.

FIG. 4 shows schematically how the line-scan camera is used to inspect the entire area of printed-circuit board 8. The area 42 sensed by the camera at any particular instant is substantially elongate, its width being typically a thousand times smaller than its length. This length, in turn, is usually much smaller than the length of the printed circuit board to be inspected. Inspection of an extended object therefore entails a relative translation between camera and object, producing the meandering path indicated by the heavy solid line in FIG. 4. Translation consists of a continuous motion along an axis perpendicular to the scanned line, followed by a stepwise translation along an axis parallel to the scanned line. This is repeated until the entire area of interest has been sensed.

The translation step along the board is somewhat shorter than the width of the "swath" cut by the line-scan camera in its pass across the board, so that a slight overlap (not shown) is produced between adjacent "swaths". The total area covered by the scan is somewhat larger in width, as well as in length, than the surface area of the printed-circuit board.

The continuous translation across the printed-circuit board is effected by the movable column 34 (FIGS. 2, 3) which carries the supporting members 30, 32, as well as the camera 10, while the stepwise translation is effected by the above-mentioned translating stage.

The invention also provides for the software correction of the optical distortion brought about by various imperfections normally found in inexpensive, mass-produced Fresnel lenses. This software correction is achieved by a one-time calibration procedure performed for each particular system, a process based on the existence in the system of a precise dimensional benchmark.

Such techniques are well known, and usually employ an array of so-called fiducial marks. These are high-contrast patterns of well defined geometry. e.g., a cross, a circle a checkerboard pattern, or a grid of lines, etc. The patterns are superimposed on the object plane at precisely known locations and are imaged by the camera. The fiducial marks are then detected in the resulting image by suitably processing the camera signal.

The deviations between the actual locations of the fiducial marks as they appear in the image and their theoretically predicted positions are used to prepare a distortion map. This map may be in the form of a set of correction terms applied for each resolution element, or pixel, in the image.

However, in the preferred embodiment described hereinunder, the calibration procedure takes advantage of the accurate translatory motion of the scanning mechanisms moving the stage supporting the printed-circuit board, and the column supporting the optical head.

The fiducial marks are reduced to two mutually perpendicular straight edges, constituted by abrupt transitions between transparent and opaque regions. Rather than using a multitude of fiducial marks, a single target containing the two edges is translated at precisely known steps relative to the camera using both object stage and column translatory motions. An effective array of fiducial marks is thus synthesized by detecting the edge position in the image signal following each stepwise translation.

The preferred embodiment offers several advantages over standard techniques: since the translation step between consecutive measurements is variable at will, the technique lends itself readily to systems having variable resolution and or magnification.

In contrast, standard calibration techniques entail preparation of separate targets for different ranges of magnification. Moreover, the advent of optical encoders and laser interferometers to monitor displacement makes possible a measurement accuracy that is potentially superior to that of any calibration target.

The calibration procedure yields two sets; of correction terms applied to each resolution element of the line-scanning camera in two orthogonal directions. The calibration terms are stored in the system's memory, and are used to correct all subsequent camera signals for dimensional errors due to optical-system distortions. That memory section in which the calibration terms are stored is designated as a look up table.

A preferred embodiment of the calibration procedure will now be described with reference to FIGS. 5 to 8.

The calibration procedure uses two edges which, as above defined, are abrupt transitions between opaque and transparent regions in the object plane. One edge. 36 (FIG. 5) should extend substantially parallel to the line scanned by the linear CCD camera 10, which will be designated in the following as the x-axis. The other edge, 38. should extend substantially parallel to the scanning direction of the object stage window 24 (in the following, for short, "object stage"), or the y-axis. The two edges are provided by a calibration target 40 mountable on the object stage.

Calibration for the x-axis distortions will now be described with reference to FIG. 5. First, the object stage and the optical head are translated until the edge 38 is sensed by the camera 10.

The exact camera element $p_o$ on which the edge is falling is calculated from the shape of the camera signal. In FIG. 5, $p_o$ denotes the area sensed by camera element $p_o$, etc., and $(x_o, y_o)$ is an edge point inside that area.

The column 34 (FIG. 2) supporting the optical head is now moved along the x-axis by a precisely known amount 1. The same edge point $(x_o, y_o)$ is now sensed by another camera sensor element, $p_1$. The process is repeated each time the optical head is moved by the same amount 1, throughout the entire field-of-view of the camera. The interval 1 is suitably chosen to adequately sample the distortion pattern of the optical system.

With reference now to FIG. 6, the set of camera elements $p_o, p_1, \ldots p_n$ is plotted against the corresponding translations $0, 1, 21, \ldots n_1$. Ideally, in the absence of distortions, all measured points should fall on a straight line. Therefore, a linear regression is performed on the set of points, e.g., by the least-squares method. The set of x-axis distortions or deviations from the calculated straight line. such as $\Delta x_1, \Delta x_2$ in FIG. 6A. suitably interpolated for all intermediate camera sensor elements, is now entered in a look-up table.

That look-up table is later used to correct all subsequent camera signal data for x-axis distortion before further processing. The foregoing calibration procedure also yields the value of the pixel size, namely the center-to-center spacing between object regions sampled by adjacent camera sensor elements.

The y-axis distortion is measured by a similar procedure. Referring now to FIG. 7, the object stage and optical head are translated such that the camera senses the edge 36.

The object stage is now scanned along the y-axis and the edge position $(x^o, y^o)$ is calculated from the camera signal for some sensor element $q_o$. The optical head is now translated by some small amount s, calculated such that the same edge point, properly accounting for x-axis distortion is being sensed by another camera sensor element $q_1$. The calculation of the appropriate translation is based on the pixel size, computed in the above-mentioned previous step. Again the object stage is scanned in y-direction and the system searches for the new apparent (possibly distorted) edge coordinate $(x_o, y_1)$. As before, the process is repeated to cover the full width of the camera field-of-view. The interval s is chosen to adequately sample the y-axis distortion.

With reference to FIG. 8 the resultant set of camera sensor elements $q_o, q_1, q_2 \ldots q_m$ (this time all equally spaced) is plotted against the corresponding (distorted) y-coordinates $y_o, y_1, y_2 \ldots y_m$. Ideally, in the absence of any errors in the system, all y-coordinates should be identical. In practice, there may be a finite rotational error of the camera, i.e. the linear sensor is not perfectly parallel to the x-axis. This effect would tend to make the linear plot somewhat slanted. Any deviation from a straight line is attributed to optical distortion.

The regression to a straight line is therefore performed identically to the x-axis case. A look-up table representing the y-axis distortions of each sensor element (such as $\Delta y_1, \Delta y_2$ in FIG. 8A) is prepared and used to correct subsequent camera signals.

For convenience, in computing the look-up tables for the x and y distortions, a fixed amount is being added to each element, to make the relative distortion zero at the center of the field-of-view.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A telecentric imaging system comprising a Fresnel lens mountable in close proximity to an object to be imaged, a source of light for illuminating said object, and an aperture stop located at least in vicinity of the back focal point of said Fresnel lens, said aperture stop being constituted by the entrance pupil of a second imaging lens, said Fresnel lens and said imaging lens being mounted such that their respective optical axes substantially coincide.

2. The imaging system as claimed in claim 1, wherein said Fresnel lens is a plastic lens.

3. The imaging system as claimed in claim 1, wherein said Fresnel lens is of a substantially rectangular shape, with the optical axis of said lens passing at least approximately through the geometrical center of said rectangular shape.

4. An optical inspection machine of the line-scanning type employing a telecentric imaging system, comprising a column capable of translatory movement, an object stage capable of translatory movement in a direction substantially perpendicular to the translatory movement of said column, a transparent window on said object stage, means to mount said object on said window an extended source of light behind said window, a line-scanning camera mounted on the head of said column, an objective lens adapted to image said object on the sensor plane of said camera, a field lens, optically coaxial with said objective lens and located in proximity to said object to be imaged and an aperture stop for said field lens, wherein said field lens is a Fresnel lens, said aperture stop is located at the back focal point of said Fresnel lens and is constituted by the entrance pupil of said imaging objective, whereby the system objective/field lens is rendered telecentric.

5. The optical inspection machine as claimed in claim 4, further comprising a calibration target for software correction of the optical distortions produced by said telecentric imaging system, said target being mountable on said object stage and comprising at least one reference mark adapted to be imaged on said line-scanning camera.

6. The optical inspection machine as claimed in claim 5, wherein said calibration target on said object stage comprises two linear reference marks in the form of two edges constituted by abrupt transitions between opaque and transparent regions of said target in the plane, a first reference edge extending in direction of said x-axis, being substantially parallel to the scanning line of said line-scanning camera, and a second reference edge extending in direction of said y-axis, being substantially parallel to the scanning direction of said object stage.

7. A method for software correction of the optical distortion produced by a telecentric imaging system including a line-scanning camera and a Fresnel lens, comprising the steps of:

mounting on an object stage of said system a calibration target comprising at least one reference mark and effecting a relative translation between said camera and said object stage in the direction of a first and a second of two intersecting axes until said reference mark is imaged on, and sensed by said camera;

calculating, from the signal produced by said camera, the camera element upon which said reference mark is imaged, and effecting a relative translatory motion between said camera and said object stage along said first axis in discrete, equal and precisely known steps, and sensing said reference mark at each step;

plotting the thus established set of camera elements against the sequence of said discrete steps, and performing on the points thus plotted a linear regression;

establishing using the regression line thus obtained as set of first-axis deviations and entering said deviations in a look-up table to be used to correct subsequent camera signals;

effecting a continuous translatory motion between said camera and said object stage in direction of said second axis until said reference mark is imaged on, and sensed by said camera:

calculating, from the signal produced by said camera, the camera element upon which said reference mark is imaged and the corresponding coordinate along second axis;

effecting a relative translatory motion between said camera and said object stage in direction of said first axis in discrete, equal and precisely known steps;

effecting a continuous relative translatory motion between said camera and said object stage in direction of said second axis following each of said first-axis translations and sensing said reference mark at each step;

plotting the thus established set of camera elements against the corresponding second-axis coordinates, and performing on the points thus plotted a linear regression and establishing using the regression line thus obtained a set of second-axis deviations and entering said deviations in a look-up table to be used to correct subsequent camera signals.

8. The method as claimed in claim 7, wherein said calibration target on said object stage comprises two linear reference marks in the form of two edges constituted by abrupt transitions between opaque and transparent regions of said target in the plane, a first reference edge extending in direction of said first axis being substantially parallel to the scanning line of said line scanning camera, and a second reference edge extending in direction of said second axis being substantially parallel to the scanning direction of said object stage.

9. The method as claimed in claim 8 wherein the reference edge scanned by said camera in a first-axis scan is said second reference edge, and the reference edge scanned by said camera in a second-axis scan is said first reference edge.

10. The method as claimed in claim 7, wherein said first axis is an x-axis, extending in direction of the scanning line of said line-scanning camera and said second axis is a y-axis, extending in a direction perpendicular to said x-axis.

* * * * *